United States Patent [19]
Arnett et al.

[11] Patent Number: 4,722,217
[45] Date of Patent: Feb. 2, 1988

[54] METHOD AND APPARATUS FOR CALIBRATING GAS MONITORS

[75] Inventors: David W. Arnett, Monument, Colo.; Andras Gedeon, Taby, Sweden; Julie A. Reichert, Aurora, Colo.; Carl Hamilton, Spanga, Sweden

[73] Assignee: The BOC Group, Inc., Montvale, N.J.

[21] Appl. No.: 920,814

[22] Filed: Oct. 17, 1986

[51] Int. Cl.⁴ .............................................. G01N 37/00
[52] U.S. Cl. ....................................................... 73/1 G
[58] Field of Search .......................................... 73/1 G

[56] References Cited

U.S. PATENT DOCUMENTS

| | | | |
|---|---|---|---|
| 4,257,439 | 3/1981 | Mayeaux | 73/1 G X |
| 4,262,522 | 4/1981 | Reich | 73/1 G X |
| 4,489,590 | 12/1984 | Hadden | 73/1 G |
| 4,534,204 | 8/1985 | Bergquist | 73/1 G |
| 4,578,986 | 4/1986 | Navorre | 73/1 G |

Primary Examiner—Tom Noland
Attorney, Agent, or Firm—Roger M. Rathbun; Larry R. Cassett

[57] ABSTRACT

A method and means is disclosed for carrying out the calibration of a gas monitor. The calibration is effected by providing a calibration gas containing a precise amount of the constituent that is measured by the gas monitor. That calibration gas is introduced into the gas monitor and passes therethrough in a closed system such that leakage of calibration gas to the surrounding environment at the inlet to the gas monitor and from the outlet of the monitor is prevented. The calibration gas is further stalled in the gas sensor chamber of the gas monitor for the operator to make necessary adjustments to the gas monitor at no flow conditions of the calibration gas.

10 Claims, 4 Drawing Figures

METHOD AND APPARATUS FOR CALIBRATING GAS MONITORS

BACKGROUND OF THE INVENTION

This invention relates to a means and method of carrying out the calibration of gas monitors.

There are today a great variety of gas monitors used particularly in the medical field in order to continuously monitor gases to and from a patient for various reasons.

In particular, during anesthesia, the gas monitors that are normally used include $O_2$ monitors, $CO_2$ monitors and also agent monitors that display the percentages of anesthetic vapor in the gases being delivered to the patient to carry out anesthesia. Such anesthetic agents include halothane, enflurane, isoflurane and are often administered concurrently with nitrous oxide, particularly during the induction period.

Such monitors are, of course, relied upon heavily in carrying out operations on the patient and therefore their accuracy must be assured. The gas monitors, however, exhibit certain drift over a period of time and therefore are recalibrated on a regularly timed sequence, that is every so many hours of use. To carry out that calibration, a calibration gas is utilized and which contains a precise known amount of the gas detected by the monitor.

As an example, a halothane agent monitor may be calibrated with a typical calibration gas comprised of 2.0 (%) percent halothane in nitrogen commercially available in 0.5 liter containers at a pressure of about 80 psig. Larger calibration gas containers are also readily available, however, for medical instruments, only small containers are generally needed. By passing that calibration gas through the instrument that monitors halothane, the operator can determine whether the monitor read-out displays the accurate percentages of halothane, and, if not, the monitor is corrected to that desired reading.

In current calibration practices, the calibration gas is introduced into an inlet in the gas monitor in a manner deliberately designed for leakage, that is, a path to ambient atmosphere is allowed in order to avoid over pressuring the gas monitor. Calibration gas is readily provided in the aforementioned pressurized containers and can harm the gas monitor if that full pressure is allowed to act upon the gas monitor sensor or internal pumping mechanism. After the calibration gas passes through the gas monitor, it is generally released to ambient atmosphere and is thus dissipated in the same surrounding atmosphere as is breathed by the personnel carrying out the calibration.

One of the drawbacks of such system, therefore is the potential hazard due to the pollution of the atmosphere in which the personnel work. The hazards of amounts of certain agents such as halothane and nitrous oxide are well known and therefore any environment in which these gases are present puts the personnel at some risk.

In addition, by merely passing the calibration gas through the gas monitor, the volume that the gas monitor actually requires to carry out an accurate calibration is probably less than is recommended to be used, thus, the excess calibration gas is wasted. Since there is no accurate determination made of the calibration gas through the gas monitor, the operator uses some judgment in the amount of calibration gas and it is assumed that such operator would prefer to err on the side of excess, that is, they will administer more calibration gas than is technically needed in order to be sure that enough was used.

One drawback with the use of calibration gases in commercially available containers is the presence, in such containers, of flow restrictors, built into the pressurized containers to reduce the flow of calibration gas therefrom. As the pressure in the container is reduced through normal use, the flow from the container is also reduced to the extent that the actual flow is not known to the operator. For example, a new container may initially provide a flow of 1.5 liters/minute but as the container is used, the flow could easily be reduced to 50 ml./min or lower. If therefore, the instrument requires 300 ml./min for accurate calibration, the pump in the gas monitor using present calibration methods will draw in atmospheric air to supplement the difference, thus causing an inaccurate calibration. By conventional means it is not possible for the operator to know precisely when the flow from the calibration gas containers is insufficient for the requirements of the instrument.

The present methods and means are therefore both wasteful of expensive calibration gas and also create potentially hazardous working conditions for the personnel that carry out the calibration of such gas monitors.

SUMMARY OF THE INVENTION

In accordance with the present invention a means and method is provided that overcomes the aforedescribed difficulties inherent in carrying out gas monitor calibration by present procedures. With the present invention, calibration is carried out by introducing the calibration gas into a closed circuit where leakage to the surrounding ambient is prevented. The inlet connection to the gas monitor is sealed and no overpressure protection is present that would vent the calibration gas to the ambient. The problem of overpressurization is thereafter prevented by introducing the calibration gas, after passage through the gas monitor, into a scavenging system commonly used in modern operating theatres; as an alternate, the overpressurization is avoided by providing a visible indication of the quantity of calibration gas that passes through the gas monitor by observing the filling of a distensible container; thus when that container is observed to be full, the calibration gas supply can be terminated. As a further alternate, both the quantity of calibration gas to be used can be observed by the distensible container as well as coupling the outlet of the gas monitor to the scavenging system, thus providing more assurance that overpressurization cannot occur to damage the instrument and yet still making certain that sufficient gas is used consistent with the calibration requirement of the instrument as well as preventing the instrument pump from drawing in atmospheric air.

Also, by utilizing a closed system, a no flow gas condition can be established when the calibration gas is stalled within the sensor of the gas monitor for a discrete period of time so that the sensor has an unimpeded sample to analyze and stabilizing its analysis.

Thus the potential hazardous pollution is prevented by created a closed system for the calibration gas, yet the problem of overpressurization that could be caused by such closed system is nullified.

The foregoing and other advantages and features of the present invention will become readily apparent from the following description.

BRIEF DESCRIPTION OF THE DRAWINGS

The invention is diagrammatically illustrated by way of example in the drawings appended hereto, in which.

DESCRIPTION OF THE PREFERRED EMBODIMENT

Figure 1:
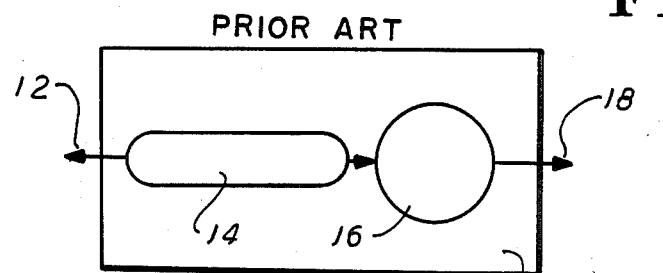
FIG. 1 is a schematic view of a typical gas monitor.

In FIG. 1 there is shown a schematic view of a gas monitor 10 illustrating only the salient features necessary in order to describe the present invention. As is typical of such sensors, there is provided an inlet 12 which receives the sample of the gas to be monitored. The present invention is particularly adapted to gas monitors used in a medical environment where the gases to be monitored include $O_2$, $CO_2$, anesthetic agents and/or nitrous oxide. In view of the pollution hazard associated with certain of these gases, the invention is most advantageous when used with an anesthetic gas monitor, including nitrous oxide.

After being admitted through inlet 12, the particular gas passes through a sensor 14 where the specific gas to be analyzed and monitored is detected. Various means are used in such anesthetic monitors to carry out detection and analysis including infrared sensing means. That sensor 14 completes the analysis of, for example, halothane anesthetic gas and the gas monitor 10 displays that concentration is some means such as by a needle gauge or digital read-out. The sample of gas to be analyzed is normally drawn through the sensor 14 by means such as a pump 16 and which also expels the gas sample out from the gas monitor 10 through an outlet 18.

Since the gas monitor 10 has been described generically as typical of such devices, it should be noted that the inlet 12 and outlet 18 may be used for the gas that passes through the gas monitor 10 during its normal function or could be a special inlet and outlet particularly adapted for a calibration gas. In either event, the gas to be analyzed passes through a sensor and is caused to be moved through the gas monitor by some pumping means.

Figure 2:
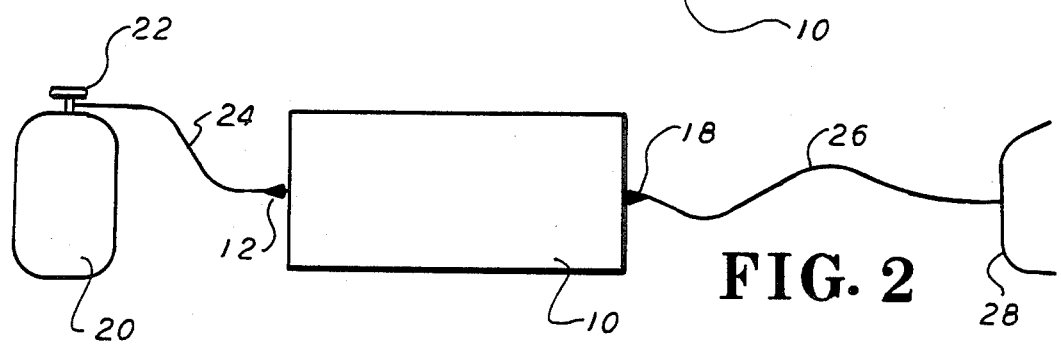
FIG. 2 is a schematic view of one of the embodiments used in carrying out the present invention.

Turning now to FIG. 2, there is shown a schematic of one embodiment of the subject invention. In that embodiment, a calibration gas container 20 is shown having a valve 22 that selectively communicates the calibration gas through tubing 24 to the inlet 12 of gas monitor 10. As previously described, such calibration gas containers are commercially available, and typically contain a volume of about 0.5 liters at a pressure of about 80 psig and contain flow restrictors. Tubing 24 is generally about five feet in length having an ID of about 0.062 in. The calibration gas moves through the gas monitor 10, is analyzed as described, and passes out the outlet 18 and continues through another tubing 26 to a closed circuit such as a gas scavenging system 28 or to the patient circuit to which a patient is connected for anesthesia. It should be noted that all of the connections of tubing 24 and 26 are gas tight such that the calibration gas basically passes through a closed system from the interior of calibration gas container 20 out through scavenging system 28. Scavenging systems are available in some hospital facilities and provide a means of the safe evacuation of hazardous gases via a central hospital system.

In carrying out the method used with the embodiment described in FIG. 2, the calibration gas container is connected without leak to the inlet 12 of gas monitor 10. The outlet 18 is connected to the gas scavenging system 28 by conventional means. Valve 22 is opened to admit calibration gas through the closed system including, of course, gas monitor 10 until a stable reading is obtained on the read-out of gas monitor 10. The calibration gas is then stalled in its passage through gas monitor 10 by turning off the pump (not shown in FIG. 2) so that a no-flow condition s obtain. The no flow condition is held for a sufficient time for the operator to carry out all of the calibration functions.

Figure 3:
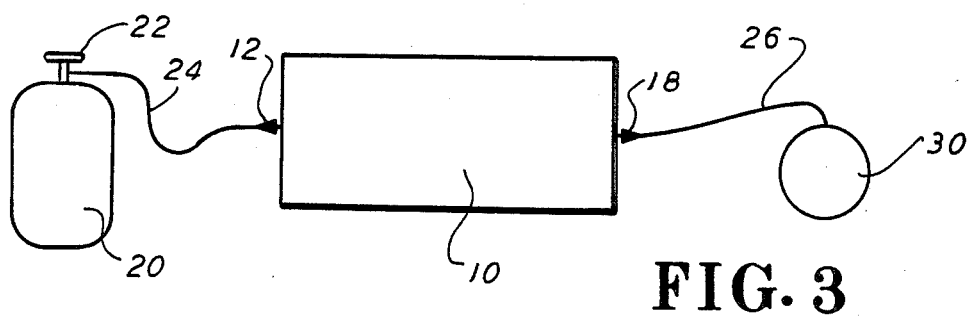
FIG. 3 is a schematic view of a further embodiment used in carrying out the present invention.

In FIG. 3, there is a schematic of further embodiment of the present invention. The components of FIG. 3 bear the same numbers and are the same as the FIG. 2 embodiment with the exception that the tubing 26 is connected to a distensible container 30 that receives the calibration gas that exits via the outlet 18. In this manner, the calibration gas still passes through a closed, leak tight system from the interior of calibration gas container 20 to the distensible container 30. Distensible container 30 serves to provide a visible indication of the volume of calibration gas that passes through gas monitor 10. The pump is continued until the distensible container 30 is filled. Preferably the distensible container 30 is a flat, flexible bag, has a small volume of about 50 ml. and is impervious to whatever agent is being monitor by the gas monitor. It is also advantageous that when deflated, the amount of gas within the flexible bag be negligible. For halothane and most other anesthetic agents, a suitable material is polyethylene.

In carrying out the method of calibration associated with the embodiment of FIG. 3, again the calibration gas container 20 is coupled to the inlet 12 of gas monitor 10 and the outlet is coupled to the collapsed distensible container 30, all connections without leak. Valve 22 is opened to allow calibration gas to pass through gas monitor 10 and into distensible container 30. The filling of distensible container 30 is observed by the operator to make sure that the distensible container 30 does not fill completely which could result in attaining too high a pressure within gas monitor 10. As the distensible container 30 reaches its full distension, the valve 22 is closed to prevent possible overpressure conditions the calibration gas container 20 is disconnected and the line vented to atmosphere. Since the distensible bag 20 is completely full, no further gas can be drawn into the gas monitor 10 and therefore the flow is stalled in the system, including, of course, gas monitor 10. The calibration gas is thus held in no flow condition until the operator can take the appropriate reading and carry out the calibration procedures. At the end of calibration procedures, the distensible container 30 can be removed without leakage of its contents and moved to an area where those contents can be safety discharged without creating a polluting hazard to personnel.

Figure 4:
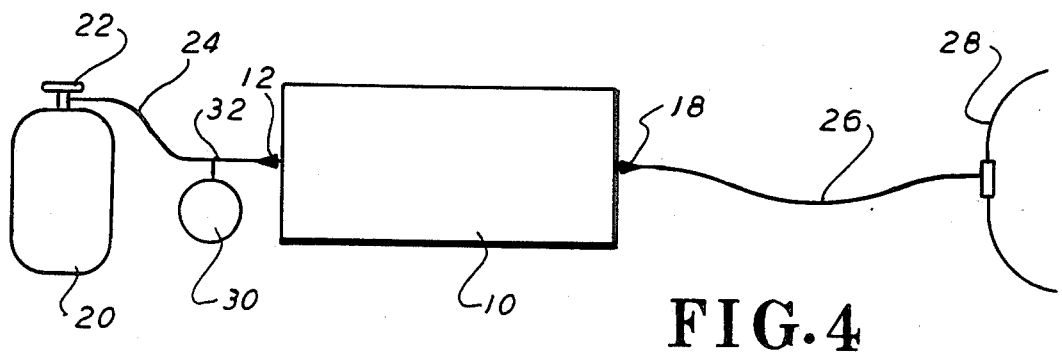
FIG. 4 is a schematic view of yet another embodiment used in carrying out the present invention.

Finally, in FIG. 4, there is a schematic of a still further embodiment of the present invention. In the embodiment, the distensible container is positioned to receive calibration gas prior to its admission to inlet 12 by means of a tee connector 32 in tubing 24. The outlet 18 is connected by tubing 26 to the scavenging system 28 as in FIG. 2 embodiment. Again, however, a closed system is provided from calibration gas container 20 to the scavenging system 28 free of leaks to the ambient atmosphere.

The method of utilizing the embodiment of FIG. 4, is again to connect the calibration gas container 20 to inlet 12 and also to connect the collapsed distensible container 30 to the tee connector 32. Outlet 18 is connected to scavenging system 28. The valve 22 is opened to allow calibration to pass through gas monitor 10 while at the same time, the distensible container 20 becomes inflated by that calibration gas. Again, the operator observes the inflation to insure that no excess pressure reaches gas monitor 10. When the distensible container 30 becomes filled, the calibration gas is turned off and the discrete sample of calibration gas then contained in the distensible container is allowed to pass through the gas monitor and contains just enough calibration gas for the operator to take a reading and make whatever calibration adjustment are necessary. When the distensible container 30 becomes deflated, the operator discontinues calibration procedures or repeats the process, thus maintaining a minmum pressure within the gas monitor.

We claim:

1. A method of calibrating a gas monitor analyzing at least one gas constituent comprising the steps of:
   a. introducing a calibration gas having a known quantity of the at least one constituent into said gas monitor while preventing the introduced calibration gas from leaking to atmosphere;
   b. passing the calibration gas through the gas monitor,
   c. receiving the calibration gas from said gas monitor and transferring the received gas to a closed system while preventing the received gas from leaking to the atmosphere,
   d. controlling the pressure of the calibration gas at all times during steps (a)-(c) to be less than a predetermined amount by monitoring the inflated state of an inflatable container communicating with the calibration gas and discontinuing the step of introducing the calibration gas when the container becomes inflated.

2. A method as defined in claim 1 wherein said inflatable container is located downstream of said gas monitor.

3. A method as defined in claim 1 including the further step of stalling the calibration gas during its passage through the gas monitor for a predetermined period.

4. A method as defined in claim 1 wherein said transferring step transfers the received gas to a scavenging system.

5. A method of calibrating a gas monitor having an inlet for receiving gas and an outlet for discharging gas and a means of analyzing at least one gas constituent as said gas moves between said inlet and said outlet comprising the steps of:
   a. providing a calibration gas having a known quantity of the at least one constituent
   b. introducing said calibration gas to the inlet of said gas monitor while preventing leakage of said calibration gas to outside atmosphere;
   c. providing an inflatable container communicating with the calibration gas before it is introduced to said inlet.
   d. providing a gas receiving system to conduct gas to a closed system;
   e. removing said calibration gas from the outlet of said gas monitor while preventing leakage of said calibration gas to outside atmosphere,
   f. conveying said removed calibration gas to a gas scavenging system while preventing leakage to the outside atmosphere; and
   g. controlling the maximum pressure of the calibration gas by observing said inflatable container and terminating step (a) when said inflatable container becomes inflated.

6. A method of calibrating a gas monitor as defined in claim 5 further including the step of discontinuing calibration of the gas monitor when said inflatable container becomes deflated.

7. Apparatus for carrying out the calibration of a gas passing through a gas monitor having an inlet and an outlet and means for moving the gas from the inlet to the outlet while analyzing at least one constituent of a gas, said apparatus comprising:
   a source of calibration gas having a known concentration of said at least one constituent;
   connector means to introduce the calibration gas to the inlet of the gas monitor in a gas tight connection;
   a distensible container for receiving gas moved through said gas monitor;
   connector means for providing a gas tight passageway from said gas monitor outlet to said closed receiver;
   control means to limit the pressure of the calibration gas to a predetermined maximum throughout its passage from said source of calibration gas to said closed receiver.

8. An apparatus as defined in claim 7 wherein said distensible container is an inflatable bag.

9. An apparatus as defined in claim 8 wherein said control means includes a valve means, said valve means operable to disconnect the source of calibration gas when said inflatable bag becomes fully inflated.

10. An apparatus as defined in claim 7 further including means to stall the flow of calibration gas during its passage though said gas monitor for a predetermined time.

* * * * *